United States Patent [19]

Coleman et al.

[11] Patent Number: 4,507,289

[45] Date of Patent: Mar. 26, 1985

[54] TREATMENT OF DIABETES AND OTHER SYMPTOMS OF HYPERCORTICOIDISM USING A SYNERGISTIC COMBINATION OF ETIOCHOLANOLONES AND ESTROGEN

[75] Inventors: Douglas L. Coleman, Seal Harbor, Me.; Norman Applezweig, New York, N.Y.

[73] Assignees: Progenics, Inc., New York, N.Y.; The Jackson Laboratory, Bar Harbor, Me.

[21] Appl. No.: 566,222

[22] Filed: Dec. 28, 1983

[51] Int. Cl.$^3$ .............................................. A61K 31/56
[52] U.S. Cl. .................................... 514/170; 514/866
[58] Field of Search ......................................... 424/240

[56] References Cited
PUBLICATIONS

C.A., vol. 74, (1971), Par. 72240d, Publication by Gasparyan et al.

Primary Examiner—Elbert L. Roberts
Attorney, Agent, or Firm—Ostrolenk, Faber, Gerb & Soffen

[57] ABSTRACT

Diabetes obesity syndromes and associated hypercorticoidism are treated with a synergistic combination of α- and/or β-etiocholanolone and an estrogen.

20 Claims, No Drawings

TREATMENT OF DIABETES AND OTHER SYMPTOMS OF HYPERCORTICOIDISM USING A SYNERGISTIC COMBINATION OF ETIOCHOLANOLONES AND ESTROGEN

CROSS-REFERENCE TO RELATED APPLICATIONS

This invention is related to the present inventors' U.S. patent application Ser. No. 515,354, filed July 19, 1983, entitled "Method for Treating Diabetes Using DHEA Compounds", and Ser. No. 566,223, filed Dec. 28, 1983, entitled "Treatment of Diabetes and Other Symptoms of Hypercorticoidism Using Etiocholanolones", both of which are hereby incorporated by reference herein.

BACKGROUND OF THE INVENTION

The major function of the adrenal gland is to regulate metabolism in the body so that an intermittent intake of food can be regulated to maintain a constant metabolite supply to the cells. This is accomplished by producing steroid hormones which can control the conversion of incoming nutrients, such as aminoacids, glucose and fats into storage depots from which they can thereafter be released or interchanged, allowing a continuous flow of optimum energy and growth factors to the cells.

The steroid hormones are divided mainly into three classes. The first is glucocorticoids (cortisol), also known as gluconeogenic or diabetogenic steroids, which can convert aminoacids into glucose for direct use or store the glucose as glycogen for later use. Cortisol can therefore have an anti-anabolic effect through the depletion of aminoacids needed for protein synthesis and a diabetogenic effect through the direct release of glucose from the glycogen store.

A glucocorticoid excess, resulting from an excess of the pituitary hormone, adrenal corticoid trophic hormone (ACTH), which controls cortisol production, causes Cushing's Syndrome, an uncommon disease. Intake of an excess amount of cortisol from pharmacological use of steroids can also cause Cushing's Syndrome or Cushingoid-like disorders (hypercorticosteroidism, nor more briefly hypercorticoidism) which are progeric in that they resemble the symptoms of the diseases of aging, e.g. obesity, hypertension, diabetes, renal stones, osteoporosis, mental disorder, menstrual disturbance, susceptibility to infection and poor wound healing.

The second category of steroids is known as the adrenal androgens. Dehydroepiandrosterone (DHEA) is the principal representative of this category. The adrenal androgens which have an anabolic action are produced with puberty, reach a peak in early adulthood and then, beyond the age of 50, decline to very low levels. Secretion of ACTH, which also controls corticosteroid production, shows no such age related fluctuation.

The third category of adrenal steroids is the mineralocorticoids (aldosterone) which control the mineral balance of the body and is partially under ACTH control in that ACTH accelerates the conversion of cholesterol to all adrenal steroids.

When the body is subjected to stress, physical or mental, e.g. injury, cold, starvation or threats, real or imagined, ACTH stimulates the adrenal cortex to produce steroids in increased amounts in order to provide the body with resources necessary for response to the stress, storage or release of glucose when needed, lipid deposition or mobilization in order to maintain the energy equilibrium of the body under conditions where extra energy may be needed and/or starvation of the cells becomes a possibility.

Under normal conditions, ACTH stimulates the adrenals to secrete both cortisol and DHEA. In the aging individual, cortisol is stimulated but DHEA is not, thus resulting in relative hypercortisolism.

It is shown in the first of said related applications that DHEA is useful in the treatment of diabetes in mutant mice and treatment of adult-onset diabetes in obese individuals. The genetic form of diabetes in mice is associated with hypercorticosteroidism. Hypercorticosteroid syndromes can occur as a result of excessive ACTH production due either to stress, hypofunction of the adrenal glands, pituitary tumors, ectopic ACTH production or administration of pharmacologic doses of cortisol.

DHEA is metabolized in the body. A major metabolite is etiocholanolone (5-$\beta$-androstan-3-$\alpha$-ol-17-one, (hereinafter referred to as $\alpha$-ET) and in normal individuals it is excreted in amounts of about 0.5 mg/100 ml. $\beta$-etiocholanolone (5-$\beta$-androstan-3-$\beta$-ol-17-one, hereinafter referred to as $\beta$-ET), is a minor metabolite in man. Even when large quantities are injected, there is a significant conversion of the 3$\alpha$ to the 3$\beta$-hydroxy compound. Kappas, et al., *The Thermogenic Effect and Metabolite Fate of Etiocholanolone in Man*, J. Clin. Endrocrin. & Metab., 18, 1043–1055 (1958). In a diabetic individual, the quantity of $\alpha$-ET excreted is significantly less than in the normal individual.

$\alpha$-ET had been considered to be an inert end product whose sole fate was conjugation and excretion until it was shown that in its free (unconjugated) state, it had highly potent pyrogenic effects when injected intramuscularly in males, less potency in females and none in other species. No febrile reaction results when $\alpha$-ET is administered intravenously, or orally, or when $\beta$-ET is administered by any route. Kappas, et al., *Thermogenic Properties of Steroids*, in Methods in Hormone Research, Dorfman Ed. Vol. 4, p. 1 (New York & London Academic Press) (1965).

The spectrum of biological significance for etiocholanolones has been extended to include the regulation of porphyrin and hemesynthesis in hepatic and erythroid cells. Granick et al., *Steriod Control of Porphyrin and Hemebiosynthesis, A New Biological Function of Steriod Hormone Metabolites*, Proc. Nat. Acad. Sci., 57:1463 (1967). $\alpha$-ET as well as other non-pyrogenic 5-$\beta$ saturated steroids are also inducers of porphyrin synthesis. Wolff, et al., *The Biological Properties of Etiocholanolone*, Ann. Int. Med., 67, 1268–1295 (1967).

Said copending Application Ser. No. 566,223 describes that the administration of $\alpha$-ET. $\beta$-ET or mixtures thereof reproduce the effects of DHEA in antagonizing the effects of hypercortisolism. The effective therapeutic amount of these compounds are considerably lower than the dosage of DHEA required for maximum effect in normalizing blood sugar and maintaining islet integrity.

The administration of estrogens also reproduce the effects of DHEA in antagonizing the effects of hypercortisolism when administered at relatively high concentrations. For example, the administration of estradiol (estra-1,3.5(10)-tri-3,17$\beta$-diol) at 50 ug. twice per week subcutaneously to chow fed male mice of about 30 grams in weight prevented hyperglycemia and islet atrophy, sustained elevated plasma and pancreatic plasma immunoreactive insulin concentrations and increased the percent granulated beta cells. However, the use of estradiol and other estrogens at such a high concentration of about 5 mg/kg is undesirable because of the estrogenic activity of these materials at such dosages. It has now been surprisingly discovered that when the estrogens are administered in a non-estrogenic effective amount in combination with α- and/or β-ET, a synergistic effect in antagonizing the effects or hypercortisolism is achieved. The synergistic effect also permits the quantity of α- and/or β-ET to be reduced from the levels required when these compounds are used in the absence of the estrogen.

It is accordingly the object of this invention to provide a new method for treating diabetes-obesity syndrome and associated hypercorticoidism and enhancing the function or by preventing the destruction of the pancreatic islet beta cells using a synergistic combination α-ET and/or β-ET and estrogen as antidiabetic and antihyperglycemic agents. This and other objects of the invention will become apparent to those skilled in this art from the following description.

SUMMARY OF THE INVENTION

This invention relates to the treatment of diabetes-obesity syndrome and resulting hypercorticoidism through the administration of a synergistic combination of α-ET and/or β-ET, and estrogen and to enhancement of the function of the pancreatic islet beta cells.

DESCRIPTION OF THE INVENTION

In accordance with the present invention, a combination of α-ET and/or β-ET, and estrogen is administered to an individual in order to treat various hyperactivity syndromes particularly diabetes and associated hypercorticoidism. The α-ET and/or β-ET are administered orally. The usual array of oral dosage forms can be used, for example, tablets can be prepared by combining the α-ET and/or β-ET with the conventionally used binders and excipients. If desired, the compounds can be administered in a finely dispersed form, for example, as a finely dispersed powder or solution which is typically mixed with the food diet. In general, the administration amount to an average 70 kilo individual will be about 12.5 to 150 mg. per day and preferably about 25 to 100 mg. Unit dosage administration forms will generally contain about 12.5-100 mg., preferably about 25-50 mg., of the compounds. When combined with the diet, the compounds are usually used in an amount of up to about 1 percent by weight thereof. The compounds can be dissolved in a suitable solvent such as acetone, which is then mixed with food and thereafter the solvent is evaporated to leave the compounds in finely dispersed powdered form thoroughly mixed throughout the food.

The estrogens which are employed in accordance with the present invention include estradiol, estrone and its conjugates, androstendiol, the 17-acetylene derivatives of estradiol, the esters of estradiol and the like. The estrogens can be administered in any of their known administration forms. In the examples set forth below, the estrogen was administered by injection but it also could be administered in any other convenient form, such as a tablet or capsule. If desired, it can be administered in the same oral composition as the α- and/or β-ET. The estrogen is employed in a non-estrogenic therapeutic effective amount which typically can be about 0.07-0.35 mg per week per 70 kilos, preferably about 0.14-0.28 mg. A single administration can be employed or the weekly dosage can be divided into twice weekly, trice weekly, etc., administrations.

The efficacy of α- and β-ET in combination with estrogen has been demonstrated in experiments with mice with diabetes-obesity condition produced by having mutant diabetes (db) gene. The severity of the diabetes depends on the background genetic factors inherent in the inbred strains in which the mutations are maintained and expressed. The mice used were C57BL/Ks-db/db mice obtained from the Jackson Laboratory of Bar Harbor, Maine. In these mice, the diabetes mutation elicits an exaggerated obesity and a severe life-shortening diabetes. This diabetes is characterized by hyperplasia and hypertrophy of the beta cells of the islets of Langerhans, followed by severe degranulation and subsequent atrophy of the islets, rising blood glucose concentrations over 400 mg/dl, and death at 5-8 months.

Male mice were used. The mice were divided into groups, one of which was fed chow alone (Old Guilford 96) and others fed the chow into which either α-ET or β-ET had been incorporated. Incorporation was effected by dissolving the compounds in acetone which was mixed with the food diet, followed by evaporation of the acetone prior to use. Estrogen in peanut oil was administered by injection subcutaneously.

The mice were weighed weekly at the time of bleeding for determination of the blood sugar concentration. Plasma immunoreactive insulin concentrations were quantified periodically during the treatment period and at the time of termination. After sacrifice, the pancreas was removed, weighed and one-half was fixed in Bouin's solution for subsequent histological study and morphometric analysis and the other half homogenized in acid-ethanol (1.5% concentrated HCl in 70% ethanol) to determine the pancreatic insulin content. Blood glucose, immunoreactive insulin (IR) concentrations and glucose tolerance tests were carried out as described in Coleman, et al, Studies with the Mutation, Diabetes, in the Mouse, Diabetologia 3: 238-248 (1967).

Normal BL/Ks mice treated with α-ET or β-ET at concentrations up to 0.1% in the diet showed no toxic effects and food consumption was normal or slightly increased, whereas the rate of weight gain was slightly diminished. Blood sugar and plasma insulin concentrations remained within the normal range. Morphological analysis typically revealed 3 to 5 well-granulated islets in each section of the pancreases. The size, distribution and extent of beta cell granulation was not affected by the dietary treatments.

The following Table I sets forth the effects of estradiol, α-ET and β-ET, and chow alone, on the diabetes syndrome in the mice which had been studied for 16 to 20 weeks after weaning, at which time they were sacrificed. In this table, the pancreatic insulin is given in standard insulin units per gram of pancreas wet weight and the granulated beta cells are given as a percent of islet area, i.e., as a percentage of the area of the islets of Langerhans. Each value set forth represents average values plus or minus the standard area of the mean for 4 to 8 individual mutant mice.

TABLE I

| Diet | Blood Sugar (mg/dl) | IRI (ul/ml) | Pancreatic Insulin (u/g) | Granulated-cells (%) |
|---|---|---|---|---|
| Chow | 443 ± 30.1 | 99.6 ± 28.9 | 0.607 ± 0.16 | 4.05 ± 1.08 |
| Estradiol (injected 50 ug twice/ | 132 ± 21.0 | 793 ± 98.4 | 6.38 ± 0.31 | 60 ± 6.78 |

TABLE I-continued

| Diet | Blood Sugar (mg/dl) | IRI (ul/ml) | Pancreatic Insulin (u/g) | Granulated-cells (%) |
|---|---|---|---|---|
| week) | | | | |
| α-ET (0.1%) | 180 ± 23 | 251 ± 34 | 5.57 ± 0.72 | 22.6 ± 5.23 |
| β-ET (0.1%) | 148 ± 20.3 | 3141 ± 394 | 13.5 ± 0.55 | 15.3 ± 6.34 |

The beneficial effects observed in any treatment include reduction in blood sugar concentration and elevation in the pancreatic insulin content and in percent granulated beta cells as shown in Table I. Increased numbers of larger and reasonably well granulated islets are consistent findings in mutants treated with the steroids, also shown in Table I. No signs of islet atrophy were ever observed.

Table I set forth above demonstrates that estradiol, α-ET and β-ET, were effective in preventing the development of severe diabetes in the BL/Ks diabetes mutants. They had little effect on the amount of food eaten or the rate of weight gained. Obesity remained a constant feature of the treated mutants and no obvious signs of toxicity were observed. The α-ET and β-ET were fully effective at 0.1%, and estradiol at 100 ug/week. Increased numbers of larger and reasonably well granulated islets were consistently found in the mice treated with a diet 0.1% by weight α-ET, β-ET and estradiol. No signs of islet atrophy were observed with these treatments. The treatments with α-ET, β-ET or estradiol converted the severe diabetes symptoms to normal while having little effect on the obesity and residual insulin resistance.

Studies were carried out to determine the beneficial effects of combined treatments of feeding α- and/or β-ET to mutant mice injected with non-therapeutic amounts of estradiol. As shown in Table II below, β-ET fed alone to the mice at 0.025% in the diet was without beneficial effect with regard to all parameters studied, while estradiol alone (10 ug. 2 times/week) was only slightly beneficial when compared to those mutant mice fed chow alone. The combined treatment with β-ET at a concentration of 0.05% in the diet and estradiol injection (10 ug. twice/week) was very effective with regard to controlling hyperglycemia, maintaining plasma and pancreatic insulin concentrations, and preventing islet atrophy. This marked beneficial effect was seen even when the concentration of β-ET was reduced to 0.025% (i.e. ¼ of the effective dose of β-ET when used alone). An additional reduction in the amount of estradiol injected at 5 ug. (twice per week) retained full effectiveness with respect to the development of most diabetes symptoms. The consumption of food in mutants on combined β-ET/estradiol regimens remained high (0.5 g/day) and typical of chow fed mutants. Pancreases from all mutants treated with β-ET and estradiol in various combinations were consistently characterized by decreased (more normal) numbers of well granulated islets which approached the size and number of that typical of normal (++) mice. The combined therapy with α-ET and estradiol, while being effective with respect to maintaining normal physiological parameters in preventing islet atrophy, did not increase the percent granulated beta cells to the same level achieved with β-ET.

TABLE II*

| Diet | Estradiol (ug) | Blood Sugar (mg/dl) | Body Weight (g) | Plasma IRI (u U/ml) | Pancreatic Insulin (U/g) | Granulated Cells % |
|---|---|---|---|---|---|---|
| Chow | 20 | 310 ± 31 | 67.2 ± 0.8 | 351 ± 83 | 1.19 ± 0.20 | 8.8 ± 1.5 |
| β-ET (0.025%) | 0 | 332 ± 9.5 | 46.4 ± 1.2** | 156 ± 11 | 0.57 ± 0.09 | 5.9 ± 1.0 |
| β-ET (0.025%) | 20 | 121 ± 7.9 | 55.1 ± 1.4 | 199 ± 52 | 5.65 ± 0.21 | 73.0 ± 1.4 |
| β-ET (0.025%) | 10 | 156 ± 7.7 | 60.7 ± 1.0 | 448 ± 59 | 2.99 ± 0.58 | 66.7 ± 6.2 |
| β-ET (0.05%) | 20 | 114 ± 11 | 58.0 ± 1.3 | 563 ± 18.1 | 8.70 ± 0.82 | 64.8 ± 7.0 |
| α-ET (0.05%) | 20 | 137 ± 7.8 | 59.9 ± 0.86 | 527 ± 113 | 2.69 ± 0.81 | 26.5 ± 6.6 |

*Mean ± area of the mean for groups of 5-8 male BL/Ks diabetes (db) mice; values obtained after sacrifice after 16 weeks of treatment.
**Maximal weight (48.2 g) was obtained after 12 weeks of treatment; decrease in body weight always occurs in chow fed mutants in the terminal stages of the diabetes.

The foregoing described results show that when estradiol injections were combined with diets containing either α-ET or β-ET, a marked synergistic effect was produced with beneficial effects being obtained with concentrations of either α-ET or β-ET at 0.05% in the diet. β-ET was found to be more effective than α-ET in these studies. The effective concentration of β-ET could be reduced to 0.025% in the diet without loss of beneficial effects. The twelve week study of treatment with dietary β-ET (0.025%) but with reduced dosage of estradiol (5 ug/week) produce identical results to that seen with estradiol at either 10 or 20 ug/week with respect to reducing blood sugar concentrations to normal.

The effects of the compounds, while beneficial, are reversible by cessation of administration of the compounds at least where the treatment has lasted up to 12 weeks. Furthermore, intervention with the treatment of the present invention has beneficial effects when introduced during any stage except the terminal stage of the diabetic cycle. The cycle is typically characterized by hyperactivity of the pancreas and hyperinsulinism followed by degeneration, then atrophy of the beta cells of the islet of Langerhans. Intervention at the early stages according to the present invention can actually avert the degeneration and atrophy, maintaining the islets in healthy condition despite continuing hyperactivity. Intervention at the later stages may reverse the process resulting in regeneration and enhancement of residual beta cell function.

A typical capsule which can be prepared according to this invention will contain 50 mg. α-ET, 0.04 mg. estradiol 50 mg. lactose, 50 mg. dicalcium phosphate, 2 mg. magnesium stearate and 10 mg. of talc. Typical tablets can contain 50 mg. 62 -ET, 0.04 mg. estradiol, 150 mg. starch, 5 mg. magnesium stearate, 10 mg. stearic acid and 40 mg. of dicalcium phosphate, or 50 mg. α-ET, 50 mg. β-ET, 0.02 mg. estradiol, 150 mg. starch, 5 mg. magnesium stearate, 10 mg. stearic acid and 40 mg. of dicalcium phosphate.

Various changes and modifications can be made in the method of the present invention without departing from the spirit and scope thereof. The various embodiments which have been described herein were for the purpose of further illustrating the invention but were not intended to limit it. Unless other otherwise specified, all temperatures are in degrees Centigrade and all parts and percentages are by weight throughout this specification and claims.

What is claimed is:

1. A method of treating diabetes syndromes and associated hypertcorticoidism which comprises administering to a mammal a diabetes and associated hypercorticoidism antagonizing effective amount of a synergistic combination of 5-β-androstan-3-ol-17-one compound and estrogen selected from the group consisting of the estradiol, estrone and its conjugates, androstendiol, the 17-acetylene derivatives of estradiol and the esters of estradiol.

2. The method of claim 1, wherein the amount of estrogen in the combination is a non-estrogenic therapeutic amount.

3. The method of claim 2, wherein said compound is 5-β-androstan-3-α-ol-17-one.

4. The method of claim 2, wherein said compound is 5-β-androstan-3-β-ol-17-one.

5. The method of claim 4, wherein said estrogen is estradiol.

6. The method of claim 2, wherein said estrogen is estradiol.

7. The method of claim 2, wherein the amount administered is about 12.5–500 mg. per 70 kilos of said compound and about 0.07–0.35 mg. of said estrogen.

8. The method of claim 7, wherein the amount is about 25–200 mg. of said compound and about 0.14–0.28 mg. of said estrogen.

9. The method of claim 1, wherein said combination is administered in combination with food.

10. The method of claim 7, wherein said combination is present in an amount up to about 1% of said food.

11. A composition for the treatment of diabetes syndrome and associated hypercorticoidism comprising a diabetes and associated hypercorticoidism antagonizing effective amount of a synergistic combination of 5-β-androstan-3-ol-17-one compound and estrogen selected from the group consisting of estradiol, estrone and its conjugates, androstendiol, the 17-acetylene derivatives of estradiol and the esters of estradiol.

12. The composition of claim 11, wherein the amount of estrogen in the combination is a non-estrogenic therapeutic amount.

13. The composition of claim 12, wherein said compound is 5-β-androstan-3-α-ol-17-one.

14. The composition of claim 12, wherein said compound is 5-β-androstan-3-β-ol-17-one.

15. The composition of claim 14, wherein the estrogen is estradiol.

16. The composition of claim 12, wherein the estrogen is estradiol.

17. The composition of claim 12 in combination with a pharmaceutically acceptable oral administration carrier.

18. The composition of claim 17, containing about 12.5–500 mg. of said compound and 0.01–0.05 mg. of said estrogen.

19. The composition of claim 18, containing about 25–200 mg. of said compound and 0.02–0.04 mg. of said estrogen.

20. The composition of claim 17, wherein said compound is 5-β-androstan-3-β-ol-17-one and said estrogen is estradiol.

* * * * *